United States Patent [19]
Torre et al.

[11] Patent Number: 6,033,371
[45] Date of Patent: *Mar. 7, 2000

[54] APPARATUS AND METHOD FOR VASODILATION

[75] Inventors: Ralph De La Torre, Brookline, Mass.; Kenton W. Gregory, West Linn, Oreg.

[73] Assignee: The General Hospital Corporation, Charlestown, Mass.

[*] Notice: This patent is subject to a terminal disclaimer.

[21] Appl. No.: 08/920,142

[22] Filed: Aug. 26, 1997

Related U.S. Application Data

[63] Continuation of application No. 08/458,488, Jun. 2, 1995, Pat. No. 5,662,590, which is a continuation of application No. 08/192,948, Feb. 7, 1994, Pat. No. 5,472,406, which is a continuation of application No. 07/770,553, Oct. 3, 1991, abandoned.

[51] Int. Cl.$^7$ .................................................. A61B 17/22
[52] U.S. Cl. .................................. 601/2; 606/15; 606/16; 606/2
[58] Field of Search ............................. 601/2, 15; 606/2, 606/3, 13–16, 128, 191, 194, 2.5; 607/88, 89; 600/439

[56] References Cited

U.S. PATENT DOCUMENTS

| | | |
|---|---|---|
| 4,334,321 | 6/1982 | Edelman . |
| 4,503,564 | 3/1985 | Edelman et al. . |

(List continued on next page.)

FOREIGN PATENT DOCUMENTS

| | | |
|---|---|---|
| 0144764 | 6/1985 | European Pat. Off. . |
| 3038445 | 5/1982 | Germany . |
| 3600713 | 7/1986 | Germany . |
| 3812841 | 11/1989 | Germany . |
| 1475680 | 4/1989 | Russian Federation . |
| WO9001300 | 2/1990 | WIPO . |
| WO9009762 | 9/1990 | WIPO . |
| WO9110403 | 7/1991 | WIPO . |
| WO9111963 | 8/1991 | WIPO . |

OTHER PUBLICATIONS

Linde et al., "Shock Waves in Solids," *Scientific America*, May 1969, pp. 83–91.

Bhatta et al., "Effects of Shielded or Unshielded Laser and Electrohydraulic Lithotripsy on Rabbit Bladder," *The Journal of Urology*, vol. 143, No. 4, pp. 857–860, Apr. 1990.

Davros et al., "Gallstone Lithotripsy: Relevant Physical Principles and Technical Issues[1]," The Department of Radiology, Brown University Medical Center, 7 pages (1991).

Van Leeuwen et al., "Noncontact Tissue Ablation by Holmium: YSGG Laser Pulses in Blood," *Lasers in Surgery and Medicine* 11:26–34 (1991).

Gourouliatos et a., *Las. Surg. Med.*, 10: 524–532 (1990).

Gregory et al., *Circulation Supp.*, 78:II, 295, Abstract 1176 (1988).

Teramura et al., *J. Neurosurgery*, 72:347A, Paper No. 814 (1990).

(List continued on next page.)

*Primary Examiner*—Brian L. Casler
*Attorney, Agent, or Firm*—Majestic, Parsons, Siebert & Hsue P.C.

[57] ABSTRACT

A method and apparatus for dilating blood vessels in vasospasm through the use of high frequency wave, e.g., hydraulic or acoustic waves. The invention is suitable to treat any vasospasm, including any vasospasm intractable to medication, including cerebral vasospasm, which currently is not susceptible to any mechanical or chemical treatments. The apparatus for dilating blood vessels includes a catheter having a fluid-filled lumen, a wave generator arranged within the catheter lumen for generating a wave front that propagates through the fluid in the lumen and is transmitted from the distal end of the catheter to propagate through the fluid in the blood vessel, and an energy source connected to the wave generator to provide energy to produce the wave front.

31 Claims, 1 Drawing Sheet

U.S. PATENT DOCUMENTS

| | | |
|---|---|---|
| 4,538,609 | 9/1985 | Takenada et al. . |
| 4,576,177 | 3/1986 | Webster, Jr. . |
| 4,589,415 | 5/1986 | Haaga . |
| 4,770,653 | 9/1988 | Shturman . |
| 4,832,024 | 5/1989 | Boussignac et al. . |
| 4,834,093 | 5/1989 | Littleford et al. . |
| 4,844,585 | 7/1989 | Culshaw et al. . |
| 4,852,567 | 8/1989 | Sinofsky . |
| 4,887,605 | 12/1989 | Angelsen et al. . |
| 4,913,142 | 4/1990 | Kittrell et al. . |
| 4,927,427 | 5/1990 | Kriauciunas et al. . |
| 4,932,954 | 6/1990 | Wondrazek et al. . |
| 4,985,028 | 1/1991 | Isner et al. . |
| 5,005,180 | 4/1991 | Edelman et al. . |
| 5,026,366 | 6/1991 | Leckrone . |
| 5,029,588 | 7/1991 | Yock et al. . |
| 5,041,121 | 8/1991 | Wondrazek et al. . |
| 5,058,570 | 10/1991 | Idemoto et al. . |
| 5,059,200 | 10/1991 | Tulip . |
| 5,069,664 | 12/1991 | Guess et al. . |
| 5,109,859 | 5/1992 | Jenkins . |
| 5,116,227 | 5/1992 | Levy . |
| 5,146,917 | 9/1992 | Wagnieres et al. . |
| 5,152,768 | 10/1992 | Bhatta . |
| 5,163,421 | 11/1992 | Bernstein et al. . |
| 5,188,632 | 2/1993 | Goldenberg . |
| 5,193,526 | 3/1993 | Daikuzono . |
| 5,217,454 | 6/1993 | Khoury . |
| 5,224,942 | 7/1993 | Beuchat et al. . |
| 5,254,112 | 10/1993 | Sinofsky et al. . |
| 5,254,114 | 10/1993 | Reed, Jr. et al. . |
| 5,300,066 | 4/1994 | Manoukian et al. . |
| 5,304,115 | 4/1994 | Pflueger et al. . |
| 5,304,171 | 4/1994 | Gregory et al. . |
| 5,324,282 | 6/1994 | Dodick . |
| 5,368,558 | 11/1994 | Nita . |
| 5,472,406 | 12/1995 | de la Torre et al. . |
| 5,662,590 | 9/1997 | de la Torre et al. . |

OTHER PUBLICATIONS

Ziskind et al., *Clin Res.*, 38:372A, "Vasodilation by Pulsed Dye Laser . . . " (1990).

Demer et al., *J. Am. Coll. Cardiol.*, 15:104A, "Artery Compliance Improve . . . "(1990).

Enhreich et al., *Nature*, 218:682–684 (1968).

Fishell et al., *Circulation Supp.*, 82: III, 2109 Abstract 0870 (1990).

APPARATUS AND METHOD FOR VASODILATION

This is a continuation of application Ser. No. 08/458,488, now U.S. Pat. No. 5,662,590, filed Jun. 2, 1995, which is a continuation of prior application Ser. No. 08/192,948, filed on Feb. 7, 1994, now U.S. Pat. No. 5,472,406, which is a file wrapper continuation of application Ser. No. 07/770,553, filed Oct. 3, 1991, now abandoned.

BACKGROUND OF THE INVENTION

This invention relates to a method and apparatus for dilating blood vessels in vasospasm.

Vasospasm is an abnormal and often persistent contraction of an artery that reduces the caliber of the artery and may critically reduce blood flow. Vasospasm can produce a partial or complete obstruction in arteries that otherwise appear completely normal. Greater or lesser amounts of dynamic or spastic constriction at the point of a fixed obstruction can create a severe reduction of flow even where the fixed obstruction itself would be clinically benign.

Vasospasm can occur spontaneously; or it may occur as the result of certain pharmacological stimuli, such as, for example, ergonovine testing; or of mechanical stimuli such as contact with a surgical instrument or a diagnostic or therapeutic catheter, for example as a complication of percutaneous transluminal catheter angioplasty (PTCA); or of environmental stimuli. Raynaud's phenomenon and Printzmetal angina are two additional forms of vasospasm. Furthermore, certain maladies such as subarachnoid hemorrhage can also lead to vasospasm. In particular, cerebral vasospasm, which is caused by subarachnoid hemorrhage, and opthalmic artery vasospasm may cause severe consequences if not treated promptly.

Various medications have been tested for the relief of vasospasms and are only partially effective. For example, vasospasm in coronary vasculature has been treated with calcium channel blockers. However, for some unknown reason that relates to the pharmacological and anatomical differences between cerebral and coronary vasculature, these drugs are ineffective against cerebral vasospasm. In addition, mechanical treatment such as balloon angioplasty is also ineffective against cerebral vasospasm.

Other non-chemical treatments, e.g., laser irradiation-induced dilation of the vessels, of vasospasm have likewise been relatively unsuccessful or plagued with various problems. For example, laser irradiation-induced dilation of blood vessels is cumbersome, may damage surrounding healthy tissue, does not use standard catheter guide wire techniques, and provides a narrow margin between the laser energy needed to cause vasodilation and that needed to perforate the vessel wall. Moreover, in those laser techniques using low level constant wave laser radiation, vasospasm resumes as soon as the radiation ceases.

Furthermore, mechanical dilation treatments, such as balloon angioplasty, are generally ineffective because, vasospasm generally resumes after the balloon is removed, and these treatments are very difficult in arteries that are hard to catheterize, e.g., the ophthalmic artery.

SUMMARY OF THE INVENTION

This invention features dilation of blood vessels in vasospasm through the use of high frequency (on the order of microseconds) waves, e.g., hydraulic or acoustic waves, and offers several advantages over known laser irradiation- or chemical-induced dilation. These advantages include greater safety by preventing damage to the blood vessel walls by the wave generator, e.g., a laser pulse, increased maneuverability, dilation over a concentric catheter guide wire, and an increased range of energy levels that may be safely used for therapy. In addition, the invention is successful for treating cerebral vasospasm, which currently is not known to be susceptible to any mechanical or chemical treatments. Furthermore, based upon animal studies done to date, we have found that vasospasm does not resume after treatment according to the invention. The method of the invention is suitable for any vasospasm, including any vasospasm intractable to medication, either functionally, or time limited.

The invention features an apparatus for dilating a fluid-filled blood vessel in vasospasm including a catheter having a lumen containing a fluid, a wave generator arranged within the catheter lumen for generating a wave front that propagates through the fluid in the lumen and is transmitted from the distal end of the catheter to propagate through the fluid in the blood vessel, and an energy source connected to the wave generator to provide energy to produce the wave front.

The wave generator of the invention may be a laser beam, e.g., a pulse, when the energy source is a laser. In preferred embodiments, this pulse has a duration of from about 10 nanosec to about 300 $\mu$sec and is of a wavelength of less than about 600 nm or greater than about 1000 nm. The laser may be, e.g., a holmium, ultra violet, or pulsed-dye visible laser.

The wave generator also may be a spark generator, ultrasound agitator, or piezoelectric agitator.

When the distal end of the catheter is open, the wave front is transmitted from the distal end of the catheter by exiting the catheter and passing into the vessel. When the distal end of the catheter is sealed with a membrane, the wave front is transmitted from the distal end of the catheter via the membrane.

In any of these embodiments, the wave may be, e.g., a hydraulic or acoustic wave.

In a preferred embodiment, the invention also features an apparatus for dilating a fluid-filled blood vessel in vasospasm that includes a catheter having a lumen containing a fluid, a laser energy conducting filament arranged axially within the catheter lumen, the distal end of the filament being positioned at a distance from the distal end of the catheter such that laser energy emitted from the filament generates a cavitation bubble within the catheter lumen that generates a wave front that propagates through the fluid in the lumen and is transmitted from the distal end of the catheter to propagate through the fluid in the blood vessel, and a laser energy source connected to the conducting filament to provide laser energy to produce the wave front.

The invention also features a method of dilating a fluid-filled blood vessel in vasospasm by propagating a wave front that induces vasodilation through a fluid in a blood vessel in need of dilation without generating a shock wave or cavitation bubble within the blood vessel.

Furthermore, the invention features a method of dilating a fluid-filled blood vessel in vasospasm by inserting a catheter into a blood vessel in vasospasm, the catheter having a lumen containing a fluid, generating a wave front in the fluid in the catheter, propagating the wave front through the fluid in the catheter, transmitting the wave front from the distal end of the catheter, and propagating the transmitted wave front through the fluid in the blood vessel to induce vasodilation.

The wave front used in this method may be generated by a laser pulse that forms a cavitation bubble within the catheter without forming a laser breakdown-induced shock wave. In addition, the wave may be generated by other wave generators noted above.

The fluid through which the wave front propagates may be, e.g., blood, a crystalloid solution such as saline or lactated Ringer's solution, or a colloid solution. When a laser is used, the fluid may be any solution that absorbs the incident laser energy. This fluid is in the catheter and, when it is something other than blood, may be infused into the blood vessel in vasospasm prior to dilation.

Other features and advantages of the invention will be apparent from the following description of the preferred embodiments thereof, and from the claims.

DETAILED DESCRIPTION

The drawings are first briefly described.

Drawings

Dilation

The invention utilizes a wave front transmitted from the end of a catheter to bring about dilation of a vessel in spasm. This wave front is created by a wave generator, e.g., a laser pulse, a spark generator, an ultrasound or piezoelectric agitator, or any other mechanism that can vaporize or displace the fluid rapidly enough to create a wave front. For example, a laser pulse may be used to produce a cavitation bubble, i.e., a vapor bubble, which expands to displace a certain fluid volume in a column inside the catheter. Any short laser pulse can be calibrated to give the appropriate dilatory wave, and the laser energy is adjusted so that a laser-induced breakdown of the fluid does not occur. Therefore, essentially no shock wave is created according to the invention. Only a hydraulic or acoustic wave is formed, which is on the order of 100 times slower than a shock wave generated by a laser-induced breakdown. The physical characteristics of this macroscopic hydraulic or acoustic wave are significantly different from a microscopic shock wave.

This displaced fluid serves to create a transient pressure increase or wave front that propagates coaxially down the catheter and is transmitted into the occluded artery. In one embodiment, the catheter is open-ended, and the wave front is transmitted from the distal end of the catheter merely by exiting the catheter and passing into the fluid filling the artery. In other embodiments, the catheter is close-ended, and the wave front strikes a membrane, e.g., a highly pliable polymer film, that transmits the wave energy to the fluid in the occluded vessel to generate a transmitted wave that continues on the outside of the catheter and propagates through the occluded vessel.

In each embodiment, no destructive shock wave or cavitation bubble is generated inside the exposed blood vessel. The only effect on the blood vessel is from the wave that is generated within the confines of the catheter and then propagates through the fluid within the vessel and dilates it for some distance beyond the distal end of the catheter.

Structure

Figure 1:
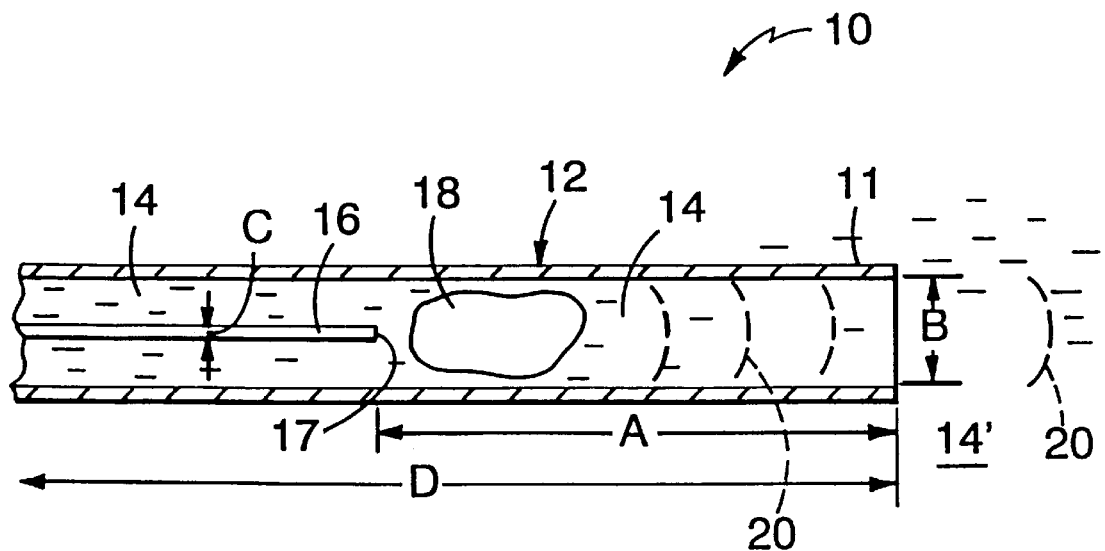
FIG. 1 is a schematic of the vasodilator of the invention.

FIG. 1 shows a laser-catheter device 10 that may be used to generate wave fronts according to the invention.

The device includes a catheter 12 with an inner diameter B and a length D. This catheter is filled with a fluid 14, e.g., blood, a crystalloid solution such as saline, or a colloid solution. In general, this fluid may be any solution capable of absorbing the incident laser energy. An optical fiber 16, with a diameter C, is located within catheter 12. The tip 17 of fiber 16 is located at a distance A from the distal end 11 of catheter 12. When a pulse of laser energy is generated by a laser (not shown), it is transmitted through fiber 16 and creates a cavitation, or vaporization, bubble 18 in fluid 14. This bubble generates a wave front 20 (represented by dashed lines in the Figures) that propagates through the liquid towards the distal end of the catheter.

Figure 2:
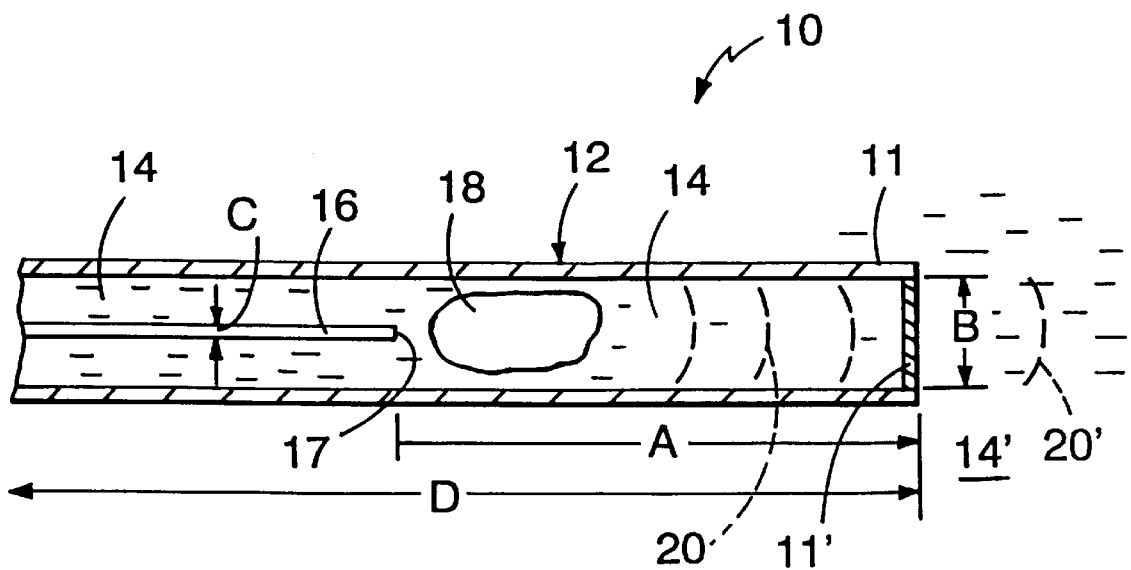
FIG. 2 is a schematic of a close-ended vasodilator.

This wave front 20 then can either exit the catheter, in the open-ended embodiments, or, as shown in FIG. 2, strike a membrane 11' that seals the distal end 11 of catheter 12. FIG. 1 shows that in the open-ended catheter, the transmitted wave front 20 is the same wave front 20 inside the catheter. FIG. 2 shows that in the sealed-end catheter, the transmitted wave front 20' differs from, but corresponds to wave front 20 inside the catheter. In both cases, the transmitted wave front propagates through the fluid 14' that surrounds the catheter and fills the vessel to be dilated. In other embodiments, the optic fiber 16 is replaced by another wave generator to create wave fronts 20.

Use of the Catheter Wave Front Generator

The dimensions and energy of the wave front are determined by selecting the dimensions A and B of the catheter and, in the laser system, dimension C of the optic fiber, as well as the duration and intensity of the laser pulse. In non-laser embodiments, energy levels of the spark from a spark gap or the ultrasound agitation may be selected by standard techniques to achieve the desired dimensions and energy levels.

In particular, the high frequency (preferably on the order of 75 to 100 $\mu$sec) wave fronts may be created via a pulsed-dye laser set to deliver a light pulse with a 15 mJ pulse of 1 $\mu$sec duration into a 200 micron fiber. This light is directed into a fluid, e.g., blood, contained well within a catheter inserted in the body (e.g., A=25–30 mm or more). Preferably, the laser pulse is from about 10 nanosec to about 300 $\mu$sec in duration and is at a wavelength of less than about 600 nm or greater than about 1000 nm. The preferred lasers for use in the invention are holmium, ultra violet, and pulsed-dye visible lasers. The preferred pulse duration for a holmium laser is about 250 $\mu$sec.

In addition, the wave front can be created through the use of an entirely extracorporeal laser delivery system, with only the catheter being inserted into the occluded artery, i.e., the dimension A being the length of the catheter section inserted into the body.

The method of using this catheter wave generator is as follows. The catheter is advanced in a blood vessel in the body to an area of vasospasm. Once the catheter is set, a wave front of short duration is launched down the center of the catheter and either exits the catheter, or is transmitted via a membrane at the end of the catheter, into the occluded vessel to effect dilation. This procedure is repeated as necessary until the full length of spasm has been dilated.

For example, a Tracker-18 Target Therapeutics (San Jose, Calif.) catheter has been used successfully, but smaller, more maneuverable catheters may also be used. In addition, larger catheters have also been used successfully, and the proper size may be easily determined by those skilled in the art depending on the application.

Animal Studies

We studied intraluminal high frequency waves in the form of hydraulic waves as a means of reversing arterial vasospasm in the rabbit model. Vasospasm was induced in 10 New Zealand white rabbit carotid arteries in vivo by application of extravascular whole blood retained in a silicon cuff. The hydraulic wave consisted of a wave front propagated in an overdamped mode with a single oscillation (average velocity 30–40 m/s; BW 200 μsec; repetition rate 2 Hz). This wave front was created in the carotid arteries with a 3 Fr laser catheter delivered via the femoral artery and coupled to a pulsed-dye laser. Carotid artery diameters were assessed by angiography and measurements made from cut films. Baseline diameters decreased by 37.5% following application of blood. Following delivery of the hydraulic wave, arterial diameter increased by a mean of 48% over spasm diameter, with no reversion to spasm diameters. Such waves delivered to control vessels not in spasm had minimal effect on their diameter (mean change of 5.3%). Scanning electron microscopy revealed no evidence of perforations or other endothelial damage. These experiments demonstrate that high frequency intraluminal wave fronts, e.g., hydraulic waves, can rapidly reverse arterial vasospasm without loss of structural or endothelial integrity of arterial walls.

Therapy

This system can be used for the treatment of any vasospasm including cerebral vasospasm, ophthalmic vasospasm, acute closure in post PTCA patients, as well as any spasm intractable to medication, either functionally, or time limited.

Other embodiments are within the following claims.

We claim:

1. A method of opening an occluded blood vessel filled with a first fluid, the method comprising the steps of:
    inserting a catheter into the blood vessel, the catheter comprising a lumen containing a second fluid, wherein the first and second fluids can be the same or different, and wherein a distal end of the lumen is covered with a membrane that separates the first and second fluids,
    generating a hydraulic wave front in the second fluid in the lumen,
    propagating the wave front through the second fluid in the lumen,
    transmitting the wave front from the distal end of the lumen and into the vessel by way of the membrane, and
    propagating the transmitted wave front through the first fluid in the blood vessel to open the occluded blood vessel.

2. The method of claim 1, wherein the wave front is generated by laser pulses communicated through an optical fiber into the lumen and absorbed by the second fluid.

3. The method of claim 2, wherein the laser pulses produce a cavitation bubble within the lumen.

4. The method of claim 2, wherein the laser pulses produce a vaporization bubble within the lumen.

5. The method of claim 1, wherein the blood vessel being opened is in vasospasm and propagating the transmitted wave front through the first fluid opens the occluded blood vessel by inducing vasodilation.

6. The method of claim 1, wherein the wave front is generated by laser pulses communicated through an optical fiber into the lumen and absorbed by the second fluid to produce a bubble within the lumen without forming a bubble within the blood vessel outside of the lumen.

7. The method of claim 6, wherein each of the laser pulses has a duration of less than 300 microseconds.

8. The method of claim 6, wherein the wave front is generated without generating a laser breakdown-induced shock wave.

9. The method of claim 1, wherein the wave front is generated by a spark, ultrasound energy, or piezoelectric agitation.

10. The method of claim 1, wherein the first and second fluids are different.

11. A method of opening an occluded blood vessel filled with a first fluid, the method comprising the steps of:
    inserting a catheter into the blood vessel, the catheter comprising a lumen containing a second fluid, wherein the first and second fluids can be the same or different,
    generating a hydraulic wave front in the second fluid in the lumen, wherein the wave front is generated by a non-laser wave generator,
    propagating the wave front through the second fluid in the lumen,
    transmitting said wave front from the distal end of the lumen, and
    propagating the transmitted wave front through the first fluid in the blood vessel to open the occluded blood vessel.

12. The method of claim 11, wherein the distal end of the lumen is open and the wave front is transmitted from the distal end of the lumen by exiting the lumen and passing into the vessel.

13. The method of claim 11, wherein the distal end of the lumen is covered with a membrane that separates the first and second fluids, and wherein the wave front is transmitted into the vessel from the distal end of the lumen by way of the membrane.

14. The method of claim 11, wherein the blood vessel being opened is in vasospasm and propagating the transmitted wave front through the first fluid opens the occluded blood vessel by inducing vasodilation.

15. The method of claim 11, wherein the wave front is generated without generating a shock wave.

16. The method of claim 11, wherein the wave front is generated by a spark, ultrasound energy, or piezoelectric agitation.

17. An apparatus for opening an occluded blood vessel filled with a first fluid, comprising:
    a catheter comprising a lumen containing a second fluid, wherein the first and second fluids can be the same or different,
    a wave generator arranged within the lumen for generating a hydraulic wave front that propagates through the second fluid in the lumen and is transmitted from a distal end of the lumen to propagate through the first fluid in the blood vessel, wherein the distal end of the lumen is sealed with a membrane and the wave front is transmitted from the distal end of the lumen via the membrane, and wherein said wave generator is controlled and located a distance from the distal end of the lumen such that no shock wave is propagated in the blood vessel, and
    an energy source connected to the wave generator to provide energy to generate the wave front.

18. The apparatus of claim 17, wherein the wave generator includes a radiation-transmitting fiber medium with one end terminating within the lumen and another end being optically connected with the energy source, wherein the energy source is a source of radiation.

19. The apparatus of claim 18, wherein the energy source includes a laser.

20. The apparatus of claim 19, wherein the laser provides electromagnetic radiation in repetitive pulses, each of which has a duration of less than 300 micro-seconds.

21. The apparatus of claim 18, wherein the radiation from the energy source is provided within the lumen and is absorbed by the second fluid, and wherein the one end of the radiation-transmitting fiber medium is positioned within the lumen to cause a bubble to be formed within the lumen as a source of the wave front.

22. The apparatus of claim 21, wherein the source of radiation includes a laser.

23. The method of claim 17, wherein the wave front is generated by a spark, ultrasound energy, or piezoelectric agitation.

24. The apparatus of claim 17, wherein the first and second fluids are different.

25. An apparatus for opening an occluded blood vessel filled with a first fluid, comprising:

a catheter comprising a lumen containing a second fluid, wherein the first and second fluids can be the same or different, a non-laser wave generator arranged within the lumen for generating a hydraulic wave front that propagates through the second fluid in the lumen and is transmitted from a distal end of the lumen to propagate through the first fluid in the blood vessel, wherein the wave generator is controlled and located a distance from the distal end of the lumen such that no shock wave is propagated in the blood vessel, and an energy source connected to the wave generator to provide energy to produce the wave front.

26. The apparatus of claim 25, wherein the distal end of the lumen is open and the wave front is transmitted from the distal end of the lumen by exiting the lumen and passing into the vessel.

27. The apparatus of claim 25, wherein the distal end of the lumen is sealed with a membrane and the wave front is transmitted from the distal end of the lumen via the membrane.

28. The method of claim 25, wherein the wave front is generated by a spark, ultrasound energy, or piezoelectric agitation.

29. An apparatus for opening an occluded blood vessel filled with a first fluid, comprising:

a catheter comprising a lumen containing a second fluid, wherein the first and second fluids can be the same or different, a wave generator arranged within the lumen for generating a hydraulic wave front that propagates through the second fluid in the lumen and is transmitted from a distal end of the lumen to propagate through the first fluid in the blood vessel, wherein the distal end of the lumen is sealed with a membrane and said wave front is transmitted from the distal end of the lumen through the membrane, and wherein the wave generator includes an optical fiber having an end terminating within the lumen, and a source of electromagnetic radiation operably connected to another end of the optical fiber and having a wavelength that is absorbed by the second fluid in a manner to create a bubble within the lumen that generates the hydraulic wave front.

30. The apparatus of claim 29, wherein the wave generator is configured and the radiation source is controlled such that no shock wave is propagated in the first fluid.

31. The apparatus of claim 29, wherein the first and second fluids are different.

* * * * *

UNITED STATES PATENT AND TRADEMARK OFFICE
CERTIFICATE OF CORRECTION

PATENT NO. : 6,033,371
DATED : March 7, 2000
INVENTOR(S) : Ralph De La Torre, et. al.

It is certified that error appears in the above-identified patent and that said Letters Patent is hereby corrected as shown below:

Title page, under UNITED STATES PATENT, item [19] replace "Torre et al." with --De La Torre et al.

Signed and Sealed this

Twenty-sixth Day of December, 2000

*Attest:*

Q. TODD DICKINSON

*Attesting Officer*      *Director of Patents and Trademarks*